(12) United States Patent
Amiot et al.

(10) Patent No.: US 11,771,502 B2
(45) Date of Patent: *Oct. 3, 2023

(54) COMPUTER-ASSISTED SURGERY SYSTEM AND METHOD

(71) Applicant: ORTHOSOFT INC., Montreal (CA)

(72) Inventors: Louis-Philippe Amiot, Montreal (CA); Éric Szmutny, Philipsburg (CA); Michel Boivin, Montreal (CA); Yannick Brosseau, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 65 days.

This patent is subject to a terminal disclaimer.

(21) Appl. No.: 17/405,165

(22) Filed: Aug. 18, 2021

(65) Prior Publication Data

US 2021/0378761 A1    Dec. 9, 2021

Related U.S. Application Data

(63) Continuation of application No. 15/361,048, filed on Nov. 24, 2016, now Pat. No. 11,116,577, which is a
(Continued)

(51) Int. Cl.
*A61B 34/20* (2016.01)
*A61B 90/00* (2016.01)
(Continued)

(52) U.S. Cl.
CPC .............. *A61B 34/20* (2016.02); *A61B 90/36* (2016.02); *A61B 90/39* (2016.02); *A61B 90/37* (2016.02);
(Continued)

(58) Field of Classification Search
CPC ......... A61B 34/20; A61B 90/36; A61B 90/39; A61B 90/37; A61B 2017/00199;
(Continued)

(56) References Cited

U.S. PATENT DOCUMENTS

| | | |
|---|---|---|
| 5,279,309 A | 1/1994 | Taylor et al. |
| 5,383,454 A | 1/1995 | Bucholz |

(Continued)

FOREIGN PATENT DOCUMENTS

| | | |
|---|---|---|
| CA | 226938 | 2/1997 |
| CA | 2439249 A1 | 9/2002 |

(Continued)

OTHER PUBLICATIONS

Kostelnik, Radoslav, Lacko, Peter, Perdock, Michal, Torok, Timotej, Ziegler, Juraj, Bielikova, Maria, Krajvocic, Tibor, BlueMedica—Wireless Medical Access Data Appliance, Department of Computer Sciences and Engineering, Faculty of Electrical Engineering and Information Technology, Slovak University of Technology, Bratislava, Slovakia.

(Continued)

*Primary Examiner* — Sanjay Cattungal
(74) *Attorney, Agent, or Firm* — NORTON ROSE FULBRIGHT CANADA LLP

(57) ABSTRACT

There is described a system and a method for assisting a user manipulating an object during a surgery, the method comprising: tracking the object in a sterile field in which surgery is being performed at a location using a tracking device which generates tracking data; processing the tracking data using a processing device located outside the sterile field to generate position and orientation information related to the object; and sending the position and orientation information related to the object to a displaying device positioned in the sterile field adjacent to the location at which the surgery is being performed, for display to the user.

14 Claims, 3 Drawing Sheets

Related U.S. Application Data continuation of application No. 12/139,751, filed on Jun. 16, 2008, now Pat. No. 9,532,848.

(60) Provisional application No. 60/944,138, filed on Jun. 15, 2007.

(51) Int. Cl.

| | | |
|---|---|---|
| A61B 17/00 | (2006.01) | |
| A61B 34/10 | (2016.01) | |
| A61B 34/00 | (2016.01) | |

(52) U.S. Cl.
CPC ............ *A61B 2017/00199* (2013.01); *A61B 2017/00221* (2013.01); *A61B 2034/102* (2016.02); *A61B 2034/105* (2016.02); *A61B 2034/2051* (2016.02); *A61B 2034/2063* (2016.02); *A61B 2034/256* (2016.02); *A61B 2090/0813* (2016.02); *A61B 2090/364* (2016.02); *A61B 2090/397* (2016.02); *A61B 2090/3925* (2016.02); *A61B 2090/3937* (2016.02)

(58) Field of Classification Search
CPC .... A61B 2017/00221; A61B 2034/102; A61B 2034/105; A61B 2034/2051; A61B 2034/2063; A61B 2034/256; A61B 2090/0813; A61B 2090/364; A61B 2090/3925; A61B 2090/3937; A61B 2090/397

See application file for complete search history.

(56) References Cited

U.S. PATENT DOCUMENTS

| | | | | |
|---|---|---|---|---|
| 5,748,767 | A * | 5/1998 | Raab | G16H 50/50 604/19 |
| 5,749,362 | A | 5/1998 | Funda et al. | |
| 5,828,770 | A | 10/1998 | Leis et al. | |
| 5,961,456 | A | 10/1999 | Gildenberg | |
| 5,967,980 | A * | 10/1999 | Ferre | G01B 7/004 606/130 |
| 5,987,960 | A * | 11/1999 | Messner | A61B 17/00 73/1.79 |
| 5,999,837 | A * | 12/1999 | Messner | G02B 21/0012 600/407 |
| 6,122,541 | A * | 9/2000 | Cosman | A61B 34/20 606/130 |
| 6,175,756 | B1 * | 1/2001 | Ferre | A61B 90/36 606/130 |
| 6,235,038 | B1 * | 5/2001 | Hunter | A61B 90/36 600/417 |
| 6,298,262 | B1 * | 10/2001 | Franck | A61B 34/20 606/130 |
| 6,341,231 | B1 | 1/2002 | Ferre et al. | |
| 6,445,943 | B1 | 9/2002 | Ferre et al. | |
| 6,470,207 | B1 * | 10/2002 | Simon | A61B 6/547 378/207 |
| 6,484,049 | B1 * | 11/2002 | Seeley | A61B 34/20 600/431 |
| 6,490,467 | B1 * | 12/2002 | Bucholz | A61B 34/20 600/407 |
| 6,490,475 | B1 | 12/2002 | Seeley et al. | |
| 6,491,699 | B1 * | 12/2002 | Henderson | A61B 34/20 606/130 |
| 6,675,040 | B1 | 1/2004 | Cosman | |
| 6,845,775 | B1 | 1/2005 | Barthes | |
| 6,978,167 | B2 | 12/2005 | Dekel et al. | |
| 7,154,398 | B2 | 12/2006 | Chen et al. | |
| 7,819,807 | B2 * | 10/2010 | Barnes | G01S 7/5208 600/443 |
| 8,255,045 | B2 * | 8/2012 | Gharib | A61B 5/24 606/41 |
| 8,335,557 | B2 | 12/2012 | Maschke | |
| 2002/0087101 | A1 * | 7/2002 | Barrick | A61B 34/20 600/587 |
| 2003/0153810 | A1 * | 8/2003 | Bertolero | A61B 90/36 600/101 |
| 2003/0181800 | A1 * | 9/2003 | Bonutti | A61B 17/8858 600/407 |
| 2004/0024309 | A1 | 2/2004 | Ferre et al. | |
| 2005/0041282 | A1 * | 2/2005 | Rudolph | G02B 21/0012 359/368 |
| 2005/0203892 | A1 * | 9/2005 | Wesley | G06F 16/258 |
| 2006/0173290 | A1 * | 8/2006 | Lavallee | A61B 34/20 600/424 |
| 2006/0257008 | A1 | 11/2006 | Nolle et al. | |
| 2007/0073137 | A1 | 3/2007 | Schoenefeld | |
| 2007/0089221 | A1 * | 4/2007 | Manzella, Jr. | A61B 90/50 2/456 |
| 2007/0268133 | A1 * | 11/2007 | Sanchez | G08B 13/2462 340/568.1 |
| 2009/0054804 | A1 * | 2/2009 | Gharib | A61B 5/7455 600/554 |
| 2013/0090568 | A1 * | 4/2013 | Gharib | A61B 5/24 600/554 |

FOREIGN PATENT DOCUMENTS

| | | |
|---|---|---|
| WO | 98/02107 A1 | 2/1998 |
| WO | 0154558 A2 | 8/2001 |
| WO | 2006119618 A1 | 11/2006 |

OTHER PUBLICATIONS

Chen, Elizabeth S., Mendonca, Eneida A., McKnight, Lawrence K., Stetson, Peter D., Lei, Jianbo, Cimino, James J., PalmCIS: A Wireless Handheld Application for Satisfying Clinician Information Needs, Journal of the American Medical Informatics Association, Oct. 5, 2003.

Overview of Wireless Architecture and Products, as found on Internet website http://www.cs.purdue.edu/homes/fahmy/reports/leynawap.htm.

Gessler, Stefan, Kotulla, Andreas, PDAs as mobile WWW browsers, Telecooperation Office, University of Karlsruhe, Germany.

Bluesocket Case Study, Planning and Operating a Wireless Authentication and Policy Management System at Harvard Medical School—Wireless at 'The Med School': Past, Present and Future, as found on Internet website www.bluesocket.com.

Principles for designing your hospital intranet, as found on Internet website http://www.handheldsfordoctors.com/learn/wireless/principles.htm.

Lai, Albert Max, Nieh, Jason, Laine, Andrew, Starren, Justin, Remote Display Performance for Wireless Healthcare Computing, proceedings of the Eleventh World Conference on Medical Informatics (Medinfo 2004), San Francisco, CA, Sep. 7, 11, 2004.

Seshadri, Krishnan, Liotta, Lance, Gopal, Rakesh, Liotta, Ty, A Wireless Internet Application for Healthcare, IEEE, 2001.

Zeadally, Sherali, Pan, Junhua, Design and Implementation of a Wireless Prescription System, proceedings of the 37th Hawaii International Conference on System Sciences, 2004.

Chen, Elizabeth S., McKnight, Lawrence K., Stetson, Peter D., Cimino, James J., Issues in Developing Clinical Applications for the Wireless Environment, proceedings of the AMIA 2002 Annual Symposium, p. 995.

Hauser, Susan E., Demner Fushman, Dina, Ford, Glenn, Thoma, George R., PubMed on Tap: Discovering Design Principles for Online Information Delivery to Handheld Computers, Communications Engineering Branch, Lister Hill National Center for Biomedical Communications, National Library of Medicine, National Institutes of Health, Department of Health and Human Services, Bethesda, MD 20894.

Friedman, Ellie, Is Your Telehealth Network Secure?, Telehealth Practice Report, v.8(1):4,10 11, 2003.

Zhao, Xiaoming, Fei, Ding Yu, Doarn, Charles R., Harnett, Brett, Merrell, Ronald, A Telemedicine System for Wireless Home Health-

(56) References Cited

OTHER PUBLICATIONS care Based on BluetoothTM and the Internet, Telemedicine Journal and e Health, No. 2004, vol. 10, No. supplement 2: S 110 S 116.
Lamberti, Fabrizio, Montrucchio, Bartolomeo, Sanna, Andrea, Zunino, Claudio, A Web based architecture enabling multichannel telemedicine applications, Dipartimento di Automatica e Informatica, Politecnico di Torino, corse Duca degli Abrussi 24, I 10129 Torino, Italy.
Wireless LAN Access Point, IEEE 802.11g, 54Mbps, User's Manual.
Cedars Sinai Medical Center Case Study, Wireless Data Access in the Clinical Environment.
Wireless Internet Enterprise Applications.
Hauser, Susan E., Demner Fushman, Dina, ford, Glenn, Thoma, George R., A Testbed System for Mobile Point of Care Information Delivery, Communications Engineering Branch, Lister Hill National Center for Biomedical Communications, National Library of Medicine, National Institutes of Health, Department of Health and Human Services, Bethesda, MD 20894.
Venkatasubramanian, K., Deng, G., Mukherjee, T., Quintero, J., Annamalai, V., Gupta, K.S., Ayushman: A Wireless Sensor Network Based Health Monitoring Infrastructure and Testbed, Department of Computer Science and Engineering, Arizona State University, Tempe, AZ 85281.
Thompson, Craig, Ford, Steve, Bannon, Tom, Pazandak, Paul, Wells, David, Agility, Object Services and Consulting, Inc. (OBJS).
Amaroli, Cristiana, Azzini, Ivano, Ferrario, Lorenza, Giorgino, Toni, Nardelli, Luca, Orlandi, Marco, Rognoni, Carla, An Architecture for a Multi Modal Web Browser, Dipartimento di Informatics et Sistemistica, Universita di Pavia, Italy, ITC irst, Pante di Povo, Trento, Italy.
BlackBerry Case Study, Care giver: BlackBerry helps local government improve social services, Cambridgeshire County Council, Public Sector, Cambridgeshire, U.K.
Coplink, A National Model for Law Enforcement Information Sharing and Knowledge Management, Artificial Intelligence Lab (ai.bpa.arizona.edu), Tucson Police Department, Phoenix Police Department, Knowledge Computing Corporation.
Fujikawa, Kazutoshi, Yamazawa, Kazumasa, Ishikawa, Tomoya, Butsuen, Yuichi, Sato, Tomokazo, Nakaramura, Yutaka, Sunahara, Hideki, Yokoya, Naokazu, A Networked Telepresence System with an Internet Automobile and Its Transmission Issue, Information Technology Center, Nara Institute of Science and Technology, Ikoma, Nara 630 0192, Japan, Graduate School of Information Science, Nara Institute of Science and Technology, Ikoma, Nara 630 0192, Japan, Graduate School of Information Science.
Portable Communications, Wearable Communications, Portable/Wearable Communications, Transportable Communications, Wireless Network Equipment, Network Management System, and Smart Antennas, by Network Anatomy, business@networkanatomy.com.
Lai Albert M., Nieh, Jason, Bohra, Bhagyashree, Nandikonda, Vijayarka, surana, Abhishek P., Varshneya, Suchita, Improving Web Browsing on Wireless PDAs Using Thin Client Computing, WWW2004, May 17, 22, 2004, New York.
Delsing, Jerker, Lindgren, Per, Ostmark, Ake, Mobile Internet Enables Sensors Using Mobile Phones as Access Network, ITcon, vol. 9 (2004), p. 381.

\* cited by examiner

COMPUTER-ASSISTED SURGERY SYSTEM AND METHOD

CROSS-REFERENCE TO RELATED APPLICATION

This application is a continuation of application Ser. No. 15/361,048, filed on Nov. 24, 2016 which claims priority on application Ser. No. 12/139,751, filed on Jun. 16, 2008. The present application also claims priority on U.S. Provisional Patent Application No. 60/944,138, filed on Jun. 15, 2007.

TECHNICAL FIELD

The present application relates to computer-assisted surgery systems and methods, and more particularly to the tracking of objects, like navigation systems in computer-assisted surgery.

BACKGROUND

Computer-assisted surgery (CAS) systems typically have a tracking device to track in space an object involved in a surgery, such as an implant or a surgical instrument. A computer system for outputting information related to the object being tracked is also generally used. Computer-assisted surgery (CAS) systems may display information about the object being tracked on a single displaying device, with or without images acquired by the CAS system.

Some more recent CAS systems involve imageless tracking as opposed to commonly used image-based systems. The displaying device is however typically located outside the surgical sterile field and away from the surgical table. With this configuration, the medical personnel involved in the surgery, or present in the room, may view the information being displayed. A user performing or involved the surgery must move his/her head and/or divert his/her sight from the surgical field of view or the location at which the surgery is being performed in order to look at the displaying device. Possible involuntary movements of the arms and hands of the user may occur at this moment and create an undesired displacement of the object being manipulated or an error in performing actions required during surgery.

The displaying device of typical CAS systems is also for the use of everyone in the operation room. The information displayed is the same for everyone and not necessarily targeted at a specific task of a specific viewer/user.

SUMMARY

It is therefore an aim of the present disclosure to provide a novel computer-assisted surgery system and method that addresses issues associated with the prior art.

According to a first embodiment, there is provided a system for assisting a user manipulating an object during a surgery, the system comprising: a tracking device for tracking the object in a sterile field in which surgery is being performed, and for generating tracking data for the object; a processing device positioned outside the sterile field, for generating tracking information related to the object by processing the tracking data received from the tracking device; and a sterilized displaying device located in a volume within the sterile field defined as being above a plane of and delimited by an operating table and below the shoulders of an operator standing next to a patient lying on the operating table, the displaying device for displaying the tracking information received wirelessly from the processing device to the user during the surgery, the displaying device having a touch-screen for interaction with the user through said processing device, the displaying device being supported directly by the operating table via a support extending between the displaying device and the operating table.

According to a second embodiment, there is provided a method for assisting a user in manipulating an object during a surgery, the method comprising: tracking the object located in a sterile field at which surgery is being performed to generate tracking data, the sterile field comprising a volume defined as being above a plane of and delimited by an operating table and below the shoulders of an operator standing next to a patient lying on the operating table; processing the tracking data from a location remote of the sterile field, to generate tracking information related to the object; and wirelessly sending the tracking information from the location remote of the sterile field for display in the volume of the sterile field to the user on a sterilized displaying device, during the surgery, the displaying device having a touch-screen for interaction with the user through said processing device, the displaying device being supported directly by the operating table via a support extending between the displaying device and the operating table.

In the specification, the term "procedure" is meant to refer to a procedure, a series of actions, steps or operations conducing to an end or a final terminating step, a set of instructions.

In the specification, the term "surgery" is meant to refer to: a procedure performed on a patient usually with instruments; the performance of a practical work or of something involving the practical application of principles or procedures; and any operative or manual procedures.

BRIEF DESCRIPTION OF THE DRAWINGS

It will be noted that throughout the appended drawings, like features are identified by like reference numerals.

DESCRIPTION OF THE PREFERRED EMBODIMENTS

Figure 1:
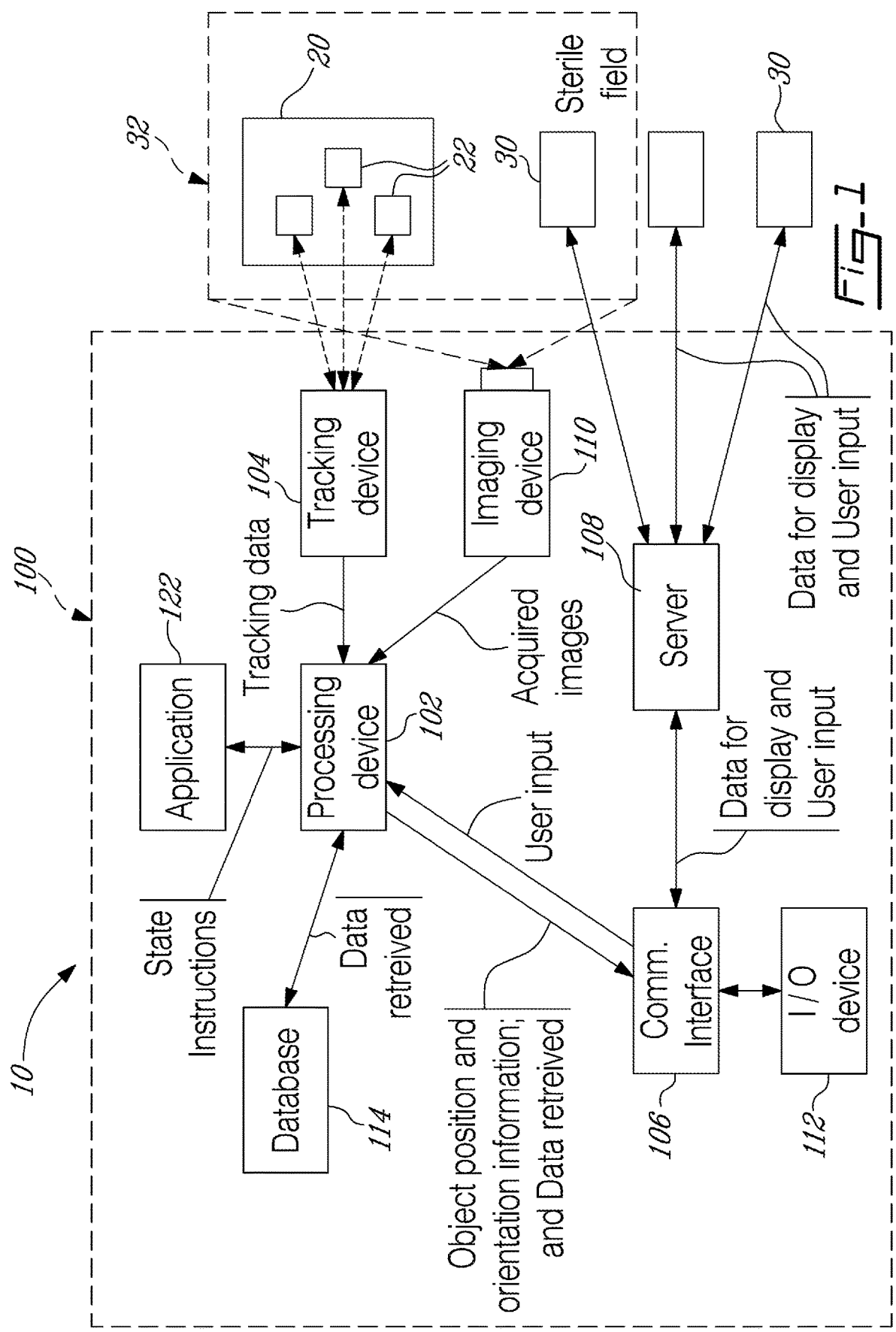
FIG. 1 is a schematic view of a computer-assisted surgery system in accordance with an embodiment.

FIG. 1 schematically illustrates the various components of the system in accordance with an embodiment.

The system 10 tracks an object or multiple objects 20 being manipulated during surgery (also generally referred to as a manipulative procedure) using markers 22. The system 10 also has displaying devices 30. At least one of the displaying devices 30 is placed within a sterile field 32.

The system 10 has a subsystem 100 depicted as a group of various components for illustrative purposes. The components may be regrouped in a unitary device or each components may form separate units.

As illustrated, the subsystem 100 has a processing device 102, a tracking device 104, a communications interface 106, and a server 108.

The subsystem 100 optionally has an imaging device 110, an input/output device 112, and a database 114.

The processing device 102 communicates with each one of the displaying devices 30, which are located in or out of a sterile field of surgery 32, via the server 108. The server 108 allows for client-server communications, the clients being each one of the displaying devices 30.

The tracking device 104 tracks an object 20 or many objects being manipulated by a user or being present within the sterile field 32 while performing the surgery. The object 20 can be an implant, a surgical instrument, a surgical tool, a reference base anchored to the patient, or any other device involved in the surgery.

The tracking device 104 detects and sends tracking data to the processing device 102. The tracking data is indicative of a position and an orientation of the object 20 in space with respect to the tracking device 104. The tracking device 104 uses passive or active markers 22 to track the object 20; these are placed in a known configuration on the object 20. The known configurations are optionally stored in a memory of the processing device 102 or in the optional database 114 for future analysis of the tracking data by the processing device 102.

Still referring to FIG. 1, the processing device 102 uses the tracking data detected by the tracking device 104, the configurations of the markers 22 and/or any additional information pertaining to the object 20 being tracked, such as a computer model of the object 20, to generate the position and orientation information of the object in space, with respect to any given reference frame. This information is then sent for display from the processing device to a location in the sterile field 32, via the server 108.

The position and orientation information sent to a display device 30 in the sterile field 32 may be accompanied by representations of bone models or of parts of the tools (for example an axis, a tip of a tool).

The position and orientation information sent for display can also take the form of numerical values, such as angles, distances, differentials, and be treated to represent values associated with the surgery being performed.

Any information sent for display in addition to the position and orientation information is optionally processed using the tracking data. For example, representations of bone models or of parts of tools used during surgery are adapted or translated into a reference frame to provide a meaningful spatial display of the information to the user.

The tracking device 104 is any type of tracking device or apparatus that can locate markers on an object 20 while the object 20 is manipulated. The location of the object 20 in time can be recorded with respect to a particular reference frame. Examples of such tracking devices include but are not limited to: mechanical frames, electro-mechanical devices, acoustic tracking devices, electro-magnetic tracking devices, optical tracking devices and radio-frequency tracking devices. The markers 22 are selected to function according to any one of the above-mentioned tracking technologies (electro-magnetic, optical, radio-frequency and ultrasound) or any other type permitting the location of the object 20 so as to be able to determine its position and orientation in time with respect to a given point in space.

Still referring to FIG. 1, the subsystem 100 optionally has an imaging device 110 for acquiring images of an area at which the execution of the surgery is being performed. These images can be stored in the database 114 or in any other memory device. When images are acquired, the processing device 102 has an optional coordinate translating device (not shown) which then translates the object position and orientation information into a coordinate system relative to the images acquired, or with respect to a reference frame compatible with the acquired images. The acquired images and the object position and orientation information can be sent for display, separately or as a unified stream, to any one of the displaying devices 30 which are located at the sterile field 32.

The imaging device 110 can be any type of imaging system or apparatus for acquiring images of the area at which surgery is being performed. Images of other areas within the sterile field 32 can also be taken, as desired. The kinds of imaging device 110 which can be used include but are not limited to: X-ray, fluoroscopy, CT-scan, magnetic resonance imaging (MRI), ultrasonography.

The optional input/output devices 112 of the system 10 are generally placed outside of the sterile field 32. An input/output device 112 can be a display screen, keyboard, keypad, touch-screen, mouse, or any other commonly known device allowing the input or the output of information from and to a given user. The data entered via the input/output device 112 is optionally stored in the database 114 or any other memory device.

An application 122 is coupled to the processing device 102 for implementing instructions in assisting a given procedure such as surgery. The application 122 is configured to implement various system states which correspond to steps involved in the procedure. Steps or system states are, for example, calibrating surgical instruments, performing a bone resection verification, positioning an implant, or any other type of procedural action.

The database 114 is optionally used to store instructions of the application 122 and/or any complementary data pertinent to the given procedure or system states. For example, the database 114 can be used to store: images acquired using the imaging device 110, generic surgery information, specific information pertaining to the various actions to be accomplished during the procedure, as well as any information pertaining to a patient, living or deceased body, onto which surgery is performed. Other data is optionally stored in the database 114, such as computer models of tools or body parts which can be used by the processing device 102 in the processing of the tracking data, in the generation of the position and orientation of the object 20 or in the treatment of any information for display. The stored data can be in the form of texts, images, animations or in any other kind of format as related to the procedure. A user can choose to access the stored data at anytime before, after or during the execution of the procedure.

The complementary data stored in the database 114 is retrieved (refer to "data retrieved" in FIG. 1) and also sent, via the server 108, at the sterile field 32, for display by any one of the displaying devices 30. The displaying devices 30 then display this data to users together with any acquired images, surgery information and the object position and orientation information from the processing device 102.

Still referring to FIG. 1, the displaying devices 30 are generally positioned adjacent to a location at which the surgery is being performed and can be portable, pocket-size computing devices, such as personal digital assistance devices (Pda), information appliances, personal communicators, handheld game consoles, ultra-mobile PCs, handheld televisions or any other type of portable displaying devices.

The displaying devices 30 optionally have an input device (not shown), such as a touchscreen, to allow a user interaction such as the entry of data. The data entered by the user is optionally stored in the database 114 or a database (not shown) of the displaying device 30 and later sent back to the processing device 102. Such entered data is also optionally used by the processing device 102 to process the tracking data or to process any information to be sent for display.

Each displaying device 30 optionally has a user interface and a communication interface (not shown). The communication interface allows a communication with the server 108. The user interface and the communication interface are optionally implemented as dedicated interfaces to a user of a particular displaying device 30. In this way, the information displayed by a particular displaying device 30 is targeted to its user and depends on the nature of the user's role or on the nature of a specific task performed by the specific user in the execution of the surgery. The dedicated interfaces of each one of the displaying devices 30 may be assigned different communication priorities establishing precedence when establishing communication with the processing device 102.

Similarly, the user interface enables the display of the acquired images and the object position and orientation information according to a preference of the specific user, or to the nature of the specific user's role and tasks. Hence, different information is displayed depending on whether the user is a surgeon, an instrument technician, a nurse or any other member of the surgical team, for instance. As an example, the server 108 may concurrently send for display information related to an implant position to a displaying device of a surgeon, and information related to an instrument assembly to a displaying device of an instrument technician.

Figure 2:
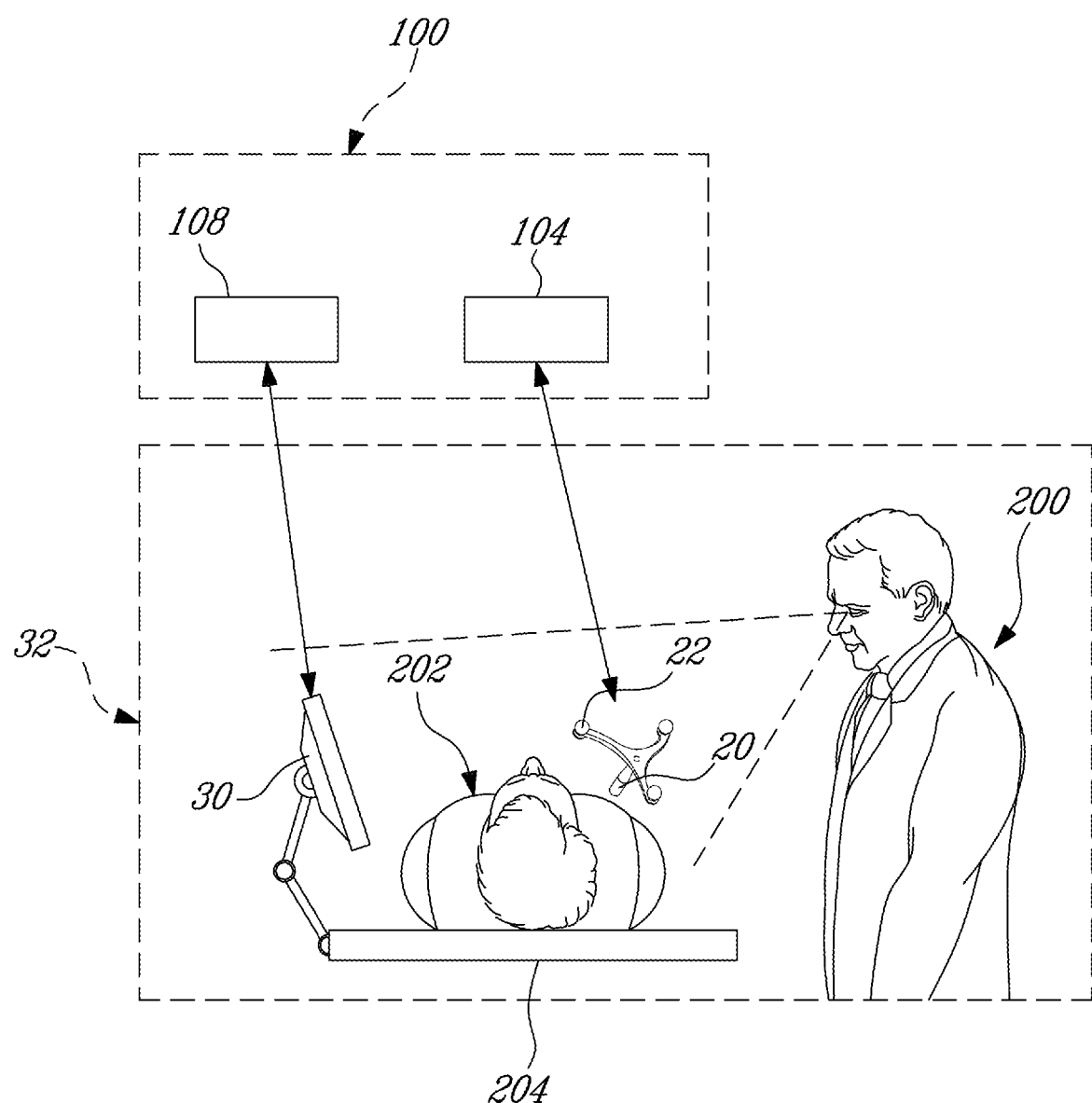
FIG. 2 is a schematic view of the computer-assisted surgery system of FIG. 1, placed within a surgery environment with the displaying device located within a sterile field for direct viewing.

FIG. 2 schematically illustrates the system 10 within the context of a surgical environment.

As shown, the sterile field 32 has a displaying device 30 located next to a body portion onto which the surgery is performed, i.e., adjacent to an area at which surgery is performed. The position of the displaying device 30 in the sterile field 32 allows the user 200 (a surgeon or a medical assistant) to access and view the displaying device 30 during surgery, and optionally within the field of view of the user while manipulating the object 20 or performing the surgery. The displaying device 30 can optionally be enclosed in a sterile bag or in any protective shield if it is not possible to properly sterilize the displaying device 30 itself.

Still referring to FIG. 2, a user 200 who is manually executing a procedure on a body portion 202 on a surgical table 204, is able to view the information displayed on the displaying device 30 without diverting his/her focus out of the sterile field 32 (or out of his/her surgical field of view). In some cases, a simple glance of the eyes of the user towards the display screen is necessary, as illustrated by the dotted lines in FIG. 2.

Referring to FIGS. 1 and 2, the server 108 is optionally a wireless bidirectional communications server. Hence, the communications interface 106 and the communications interface (not shown) of the displaying devices 30 are optionally adapted to permit wireless transmission and reception.

Displaying devices 30 such as portable display assistants (PdAs), for example, can support wireless transmission over radio-frequency and Bluetooth standards. Displaying devices 30 are also optionally equipped to support infrared data transmission and reception. Optical communication is thus optionally established between the displaying devices 30 and the interface 106, which in this case is made to support such communication. Other suitable communication protocols, systems, and devices are also used.

Wireless communications between the processing device 102 and each client displaying device 30 help in preserving the sterile field 32 effectively sterile and allow the displacement of the displaying devices 30 according to the needs of a particular procedure, the desires of a particular user, or the nature of a particular user's role or task in the procedure.

Still referring to FIGS. 1 and 2, multiple displaying devices 30 are optionally located throughout the surgery room, with at least one displaying device 30 placed within the sterile field 32 as illustrated.

When there are many users 200, each having their own dedicated displaying device 30, the communication interface 106 optionally has a security device (not shown) for assigning priorities to each communication from or to a particular displaying device 30 to or from the processing device 102.

For example, the security device implements a scheme which ensures that a surgeon who is performing a surgery has the highest priority. In this way, the surgeon is able to indicate to the processing device 102 whether or not a given step in the surgery is ready to be started or whether it is completed. In place of the security device, the security scheme may be ensured by the server 108 and each one of dedicated interfaces of the displaying devices 30.

Such a communication scheme is optionally adapted to be used to train personnel and communicate with other users 200 throughout the surgery room. For example, the head surgeon's input can provide particular training information which is then sent to other displaying devices 30 dedicated to assistant users. Each one of the users can also contact anyone located outside the surgery room for external assistance.

Figure 3:
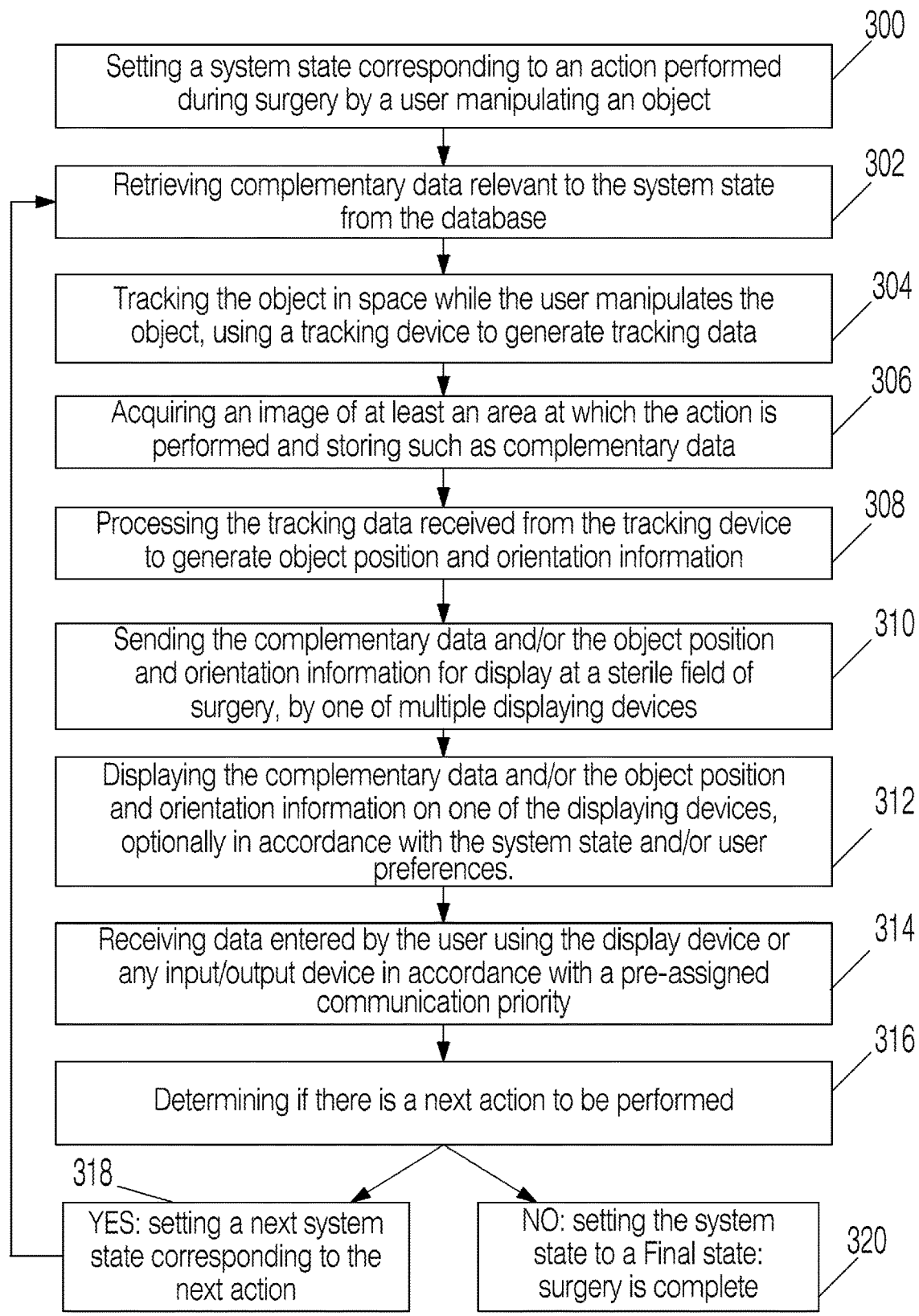
FIG. 3 is a block diagram showing steps of the method in accordance with another embodiment.

The priority scheme is also adaptable to prevent conflicts between the displaying devices 30 of various users when simultaneously trying to communicate with the processing device 102, and/or to allow or block certain communications during critical steps. FIG. 3 shows the various steps of the method, in accordance with a second embodiment. The following description of the steps in FIG. 3 involves numeral references as illustrated in FIGS. 1 and 2.

In step 300, a system state is set. The system state corresponds to an action performed during the surgery by a user manipulating an object for example. The system state may be set by a user coordinating the procedure or any other user. Alternatively, the user optionally enters a procedure name. In any case, the client terminal (such as a displaying device 30 as shown in FIG. 1) or an input device (such as device 112 in FIG. 1) can be used for such purposes. This step is optional.

In step 302, complementary data relevant to the set system state is retrieved from a memory device such as database 114 (refer to FIG. 1). This step can be accomplished by the processing device 102 (refer to FIG. 1). Alternatively, a list of steps and other information pertaining to the procedure name entered by the user is retrieved. This step is also optional.

In step 304, an object manipulated by the user to perform the action is tracked in space using a tracking device to generate tracking data. This is done in real-time throughout the method, while the surgery is being performed. In reference to FIG. 1, the tracking device 104 measures and generates tracking data optionally taken using markers 22 placed at known locations with respect to the object 20.

Now referring back to FIG. 3, in step 306, an image of at least an area at which the action is performed is optionally acquired. This step can be accomplished at anytime during the method illustrated, pre-operatively or intra-operatively, although an intra-operative image acquisition would provide for a real-time imaging of the procedure to the user. The imaging device used for this step (such as device 110 in FIG.

1) may store the images or data stream acquired on any storing device to be used by the system as complementary data.

In step 308, the tracking data received from the tracking device (device 104 in FIG. 1) is processed using any processor such as the processing device 102 (refer to FIG. 1). The data is processed to determine and generate information on a position and an orientation of the object.

In step 310, at least the object position and orientation information is sent for display at a sterile field of surgery, to anyone of the various client terminals (such as the displaying devices 30 as seen in FIG. 1), via a server.

The processing device such as device 102 in FIG. 1, optionally sends with the object position and orientation information, complementary data such as images or any data relevant for the procedure, including information pertaining to the system state, or any other data stored in a database accessible by the processing device. Once the data sent is received by a client terminal (or anyone of the displaying devices 30 illustrated in FIG. 1) located in the sterile field 32, the data is displayed in the following step 312. The information sent for display to a given client terminal is optionally dedicated information targeted at a specific user of the given client terminal. Such dedicated information may depend on the specific user's preferences, tasks, and role.

If complementary data such as images taken during surgery are also sent for display, the processing device optionally translates the object position and orientation information into a coordinate system compatible with the images. The translation into a common reference frame can alternatively be performed in step 312, once the data is received at the sterile field.

In step 312, anyone of the client terminals receive the complementary data and/or object position and orientation information, and displays this information. The client terminals can each have a different interface and the display of the information and/or complementary data is optionally altered in accordance with the system state, the preferences, the role and the tasks of a specific user of the client terminal. For example, if the system state is set for a calibration of an object, such as various tools or surgical instruments, the client terminals can display the information and/or complementary data in a window specifically designed to faciliate the action, optionally illustrating a given reference frame used.

Step 312 is performed during the surgery, optionally in real-time, and while each user executes his/her role and related tasks in order to complete the action, using the assistance of the information displayed on his/her client terminal.

In step 314, the user optionally inputs data using his/her client terminal or any other input/output device. The information entered may indicate a progression in the execution of the action, may be related to the procedure itself, the patient or the body upon which surgery is performed, the object being tracked or any other relevant information. In this step, the data entered by the user is received by the processing device of the system via a server.

When there is a plurality of client terminals, each terminals is optionally assigned a communication priority whereby a precedence is established for allowing communication between each one of the client terminals and the main processing device. Such a communication priority can be implemented using any kind of arbitration process, with each one of the client terminals having a recognizable dedicated interface.

In step 316, when the user-entered data of step 314 indicates that the action is complete or when the system determines that the action is completed from the object position and orientation information and/or the acquired images, the processing device 102 evaluates whether there is a next action to be completed. If yes, the method goes to step 318; if NO, the method goes to step 320.

In step 318, the system state is set to a next system state corresponding to a next action in the procedure. The method therefore returns to step 302.

In step 320, the system state is set to a Final state; the procedure is completed.

Steps 316-320 are replaceable by a step such as step 300, wherein the user overrides the system by setting a given system state of his/her own choosing. Changing the system state can thus be achieved at any time during the method. A pre-assigned right to change system states can be given to a specific user in order to avoid multiple users to vary the state concurrently. Other authorization schemes can be implemented.

In the above method, it is understood that some of the steps may be performed concurrently and in a variety of ways. The method involves the communication between the processing device 102 (refer to FIG. 1), located in a non-sterile field, and client terminals (refer to the displaying devices 30 of FIG. 1) which are located in a sterile field, in order to assist a user in manipulating an object during a procedure.

Additionally, information valuable to the execution of the procedure is optionally transmitted to anyone of the client terminals such that the users are well informed of the tasks at hand. The client terminals can communicate with the processing device via a server, any information pertaining to the procedure as entered by a user. The client terminals can also communicate with one another and be used to contact external assistance or external systems optionally via the server and the processing device.

It is thus understood that several other embodiments of the system and method for assisting a procedure can be implemented, and thus fall within the scope of the present invention. The embodiments of the invention described above are therefore intended to be exemplary only. The scope of the invention is intended to be limited solely by the scope of the appended claims.

The invention claimed is:

1. A system for assisting an object manipulation in a sterile field during a surgery, the system comprising:
   a tracking device for tracking at least the object relative to a bone while the at least one object and the bone are in a sterile field in which surgery is being performed, and for generating tracking data for the object;
   at least one processing device positioned inside or outside of the sterile field, for generating tracking information related to the object by processing the tracking data received from the tracking device;
   a sterilized displaying device located in a volume within the sterile field defined as being above a plane of an operating table, the volume being delimited by a periphery of the operating table, the displaying device for displaying the tracking information received from the processing device to the operator during the surgery, the displaying device having a touch-screen located in the volume for interaction with the operator; and
   a support connected to the displaying device and positioning the displaying device over the operating table and into said volume of the sterile field.

2. The system as in claim 1, wherein the displaying device is positioned within a same field of view as a location at which the surgery is being performed from a surgeon's viewpoint, for display of the information to the surgeon during manipulation of the object.

3. The system as in claim 1, further comprising an imaging device for acquiring images of at least one of the object and a location at which the surgery is being performed, the displaying device displaying the images.

4. The system as in claim 3, wherein the processing device comprises a coordinate translating device for translating the object position and orientation information into a coordinate system relative to the images.

5. The system as in claim 1, wherein the displaying device is integral to a portable handheld computing device in said volume during the surgery.

6. The system as in claim 5, wherein the at least one processing device is integral to the portable handheld computing device.

7. The system as in claim 1, wherein the displaying device includes multiple displaying devices each including a dedicated user interface, with at least one said displaying device in the sterile field.

8. The system as in claim 7, wherein each of the displaying devices are dedicated to a specific role.

9. The system as in claim 7, further including a communications interface for assigning a communication priority between one of the displaying devices and the processing device, the communication priority being in accordance with the dedicated user interface involved in the communication.

10. The system as in claim 1, further including a database for the at least one processing device, the database storing information on at least one of the surgery, the object and the location, the information for being displayed by the displaying device.

11. The system as in claim 1, wherein the tracking device comprises markers placed on the object, the markers for being tracked using one of: a mechanical frame, an electro-mechanical device, an acoustic device, an electro-magnetic device, an optical device and a radio-frequency device.

12. The system as in claim 1, wherein the at least one processing device and the sterilized displaying device have transmitters for wireless communication therebetween.

13. The system as in claim 1, wherein the support is integral to the operating table.

14. The system as in claim 1, wherein the at least one processing device has a transmitter for wireless communication with at least one server of the system for additional computing to be performed by the at least one server.

* * * * *